(12) United States Patent
Bacher et al.

(10) Patent No.: US 6,419,688 B1
(45) Date of Patent: Jul. 16, 2002

(54) MEDICAL TUBULAR-SHAFT INSTRUMENT

(75) Inventors: Uwe Bacher, Tuttlingen; Fridolin Anders, Immendingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/631,194

(22) Filed: Aug. 2, 2000

Related U.S. Application Data

(63) Continuation of application No. PCT/EP99/08399, filed on Nov. 3, 1999.

(30) Foreign Application Priority Data

Dec. 4, 1998 (DE) .......................... 198 55 968

(51) Int. Cl.[7] .............................. A61B 17/28
(52) U.S. Cl. ............................ 606/205; 606/170
(58) Field of Search ...................... 606/1, 205–208, 606/170, 174, 167, 180; 604/22

(56) References Cited

U.S. PATENT DOCUMENTS

| | | | |
|---|---|---|---|
| 4,649,919 A | 3/1987 | Thimsen et al. | 604/22 |
| 4,944,093 A | 7/1990 | Falk | 606/174 |
| 4,977,900 A | 12/1990 | Fehling et al. | 128/751 |
| 4,982,727 A | 1/1991 | Sato | 128/4 |
| 5,007,917 A | 4/1991 | Evans | 606/170 |
| 5,344,428 A | 9/1994 | Griffiths | 606/205 |

FOREIGN PATENT DOCUMENTS

| | | |
|---|---|---|
| DE | 7332292 | 11/1973 |
| DE | 7330291 | 12/1973 |
| DE | 38 00 331 C2 | 5/1991 |
| DE | 295 12 503 U1 | 11/1995 |
| DE | 195 20 717 A1 | 12/1996 |
| EP | 0 688 535 A1 | 5/1995 |
| WO | WO 98/37818 | 9/1998 |

*Primary Examiner*—Kevin Truong
(74) *Attorney, Agent, or Firm*—St. Onge Steward Johnston & Reens LLC

(57) ABSTRACT

A medical tubular-shaft instrument has an elongated tubular shaft, at least one movable tool at the distal end, furthermore at least one movable grip element at the proximal end, and lastly an elongated force transmitting element. A distal end of the force transmitting element is operatively connected to the at least one tool and a proximal end of the force transmitting element to the at least one movable grip element. The force transmitting element extends through the tubular shaft. The force transmitting element, at least in its region extending through the tubular shaft and at least locally, reaches radially at at least three circumferential points as far as an inner wall of the tubular shaft and between the three circumferential points has a clearance from the inner wall, and in its remaining segments extending through the tubular shaft has a clearance from the inner wall at least over part of its circumference.

10 Claims, 3 Drawing Sheets

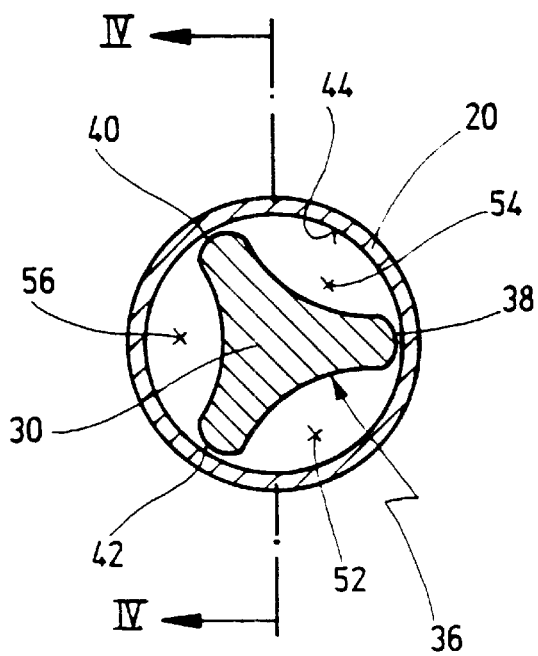
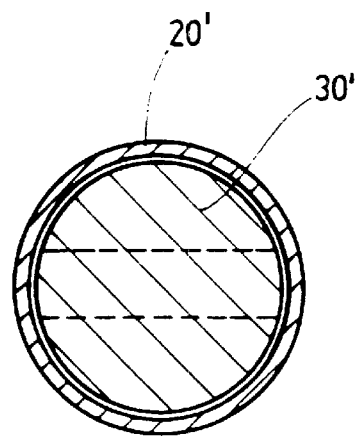
Fig. 2
Fig. 3
(STAND DER TECHNIK)
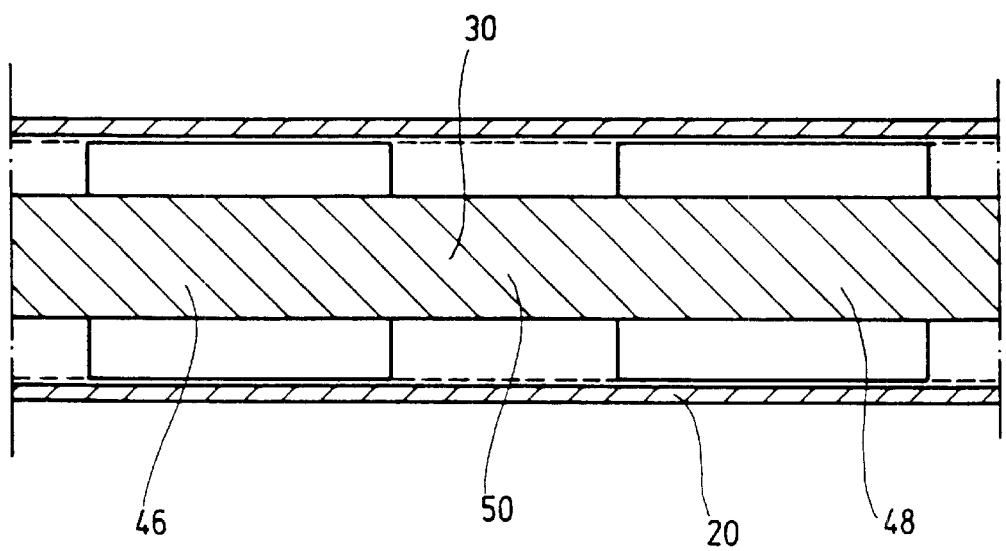
Fig. 4

MEDICAL TUBULAR-SHAFT INSTRUMENT

CROSS REFERENCE TO PENDING APPLICATION

This is a continuation of pending International application PCT/EP99/08399 filed Nov. 3, 1999, which designated the United States.

BACKGROUND OF THE INVENTION

The present invention generally relates to a medical tubular-shaft instrument. The present invention relates to a medical instrument of the kind, which generally comprises an elongated tubular shaft, at least one movable tool at the distal end, further at least one movable grip element at the proximal end, and lastly an elongated force transmitting element, the distal end whereof is operatively connected to the at least one tool and the proximal end whereof to the at least one movable grip element, the force transmitting element extending through the tubular shaft.

Tubular-shaft instruments of this kind are used in minimally invasive surgery as surgical instruments, in order to perform surgical procedures through a small incision in the body under endoscopic monitoring. These tubular-shaft instruments are equipped with different functions for different surgical procedures that are to be performed in the human or animal body.

A "tubular-shaft instrument" for the purposes of the present invention is thus understood to be, for example, a forceps for cutting and/or grasping and/or, for example, also a needle holder. The at least one tool can thus be configured, for example, in the form of a movable jaw part that has a blade which coacts in cutting fashion with a blade of a second movable or stationary jaw part. In the case of a needle holder, the at least one movable tool has a configuration which makes it possible with that tool to hold a needle in the surgical field and to guide it in order to create a suture so as to join tissue.

For actuation of the at least one movable tool, there is provided at the proximal end of the tubular-shaft instrument at least one movable grip element that is operatively connected to the at least one movable tool via an elongated force transmitting element, for example in the form of a pull rod. A movement of the movable grip element thus brings about a movement of the at least one movable tool at the distal end of the tubular shaft in order to perform the corresponding function, for example cutting or holding and guiding the needle through the tissue.

In the context of minimally invasive surgery, it is occasionally necessary to configure such tubular-shaft instruments with a tubular shaft diameter that is approximately 3 mm or less. Such small tubular shaft diameters are desirable, for example, for surgery on small children or also for procedures in specific surgical areas, for example in the head region.

With the known tubular-shaft instruments, in particularly those having a diameter of approximately 3 mm or less, the force transmitting element is adapted in terms of its diameter to the inside diameter of the tubular shaft, i.e. the outside diameter of the force transmitting element is approximately the same as the inside diameter of the tubular shaft, so that the force transmitting element completely fills up the interior of the tubular shaft.

The disadvantage of this configuration is that when the force transmitting element is in place, the interior of the tubular shaft cannot be adequately flushed, since sufficient passage for a flushing liquid is not present between the force transmitting element and the tubular shaft. Since, however, such miniaturized tubular-shaft instruments cannot be disassembled, or at least cannot easily be disassembled, in such a way that the force transmitting element can be removed from the tubular shaft for cleaning—since the join between the at least one movable tool and the force transmitting element on the one hand, and the force transmitting element and the at least one movable grip element on the other hand, is not detachable or not easily detachable—this means that the known tubular-shaft instruments cannot be adequately cleaned. Contaminants that collect in the interior of the tubular shaft during an operation therefore cannot be removed to the point that these tubular-shaft instruments can meet stringent sterility and hygiene requirements.

In order to improve the cleaning properties of these tubular-shaft instruments, consideration has been given to equipping the force transmitting element with an outside diameter that is less than the inside diameter of the tubular shaft, so that a sufficient flushing space remains between the force transmitting element and the tubular shaft. It has proven to be particularly disadvantageous in this context, however, that despite its rigid configuration, the tubular shaft bends in response to tensile forces transferred from the force transmitting element to the at least one movable tool. The tubular-shaft instrument becomes unusable, however, if the tubular shaft is bent. The same disadvantageous effect also occurred if, instead of a small-diameter force transmitting element with a round cross section, a tension strip flattened on both sides was used. A force transmitting element in the form of a flat tension band also resulted in a loss of stability in the tubular shaft.

It is therefore the object of the invention to develop a tubular-shaft instrument of the kind cited initially in such a way that the tubular-shaft instrument can easily be cleaned, by flushing the interior of the tubular shaft, while the force transmitting element is in place, whereas the stability of the tubular-shaft instrument against bending of the tubular shaft continues to be guaranteed.

SUMMARY OF THE INVENTION

According to the present invention this object is achieved, by a tubular-shaft instrument, comprising an elongated tubular shaft having a distal end and a proximal end, and having an inner wall; at least one tool disposed at said distal end of said shaft; at least one movable grip element disposed at said proximal end of said shaft; an elongated force transmitting element having a distal end which is operatively connected to said at least one tool, and a proximal end which is operatively connected to said at least one movable grip element, said force transmitting element extending through said tubular shaft, wherein said force transmitting element, at least in its region extending through said tubular shaft and at least locally, reaches radially at at least three circumferential points as far as said inner wall of said shaft and between said three circumferential points has a clearance from said inner wall, and in its remaining portions extending through said tubular shaft has a clearance from said inner wall at least over part of its circumference.

What is thus provided according to the present invention is firstly that the force transmitting element, at least in its region extending through the tubular shaft, continuously has, at least over part of its circumference, a clearance from the inner wall of the tubular shaft, so that the interior of the tubular shaft has a flushing cross section sufficient for cleaning even when the force transmitting element is in place. Also provided according to the present invention is that the force transmitting element, at least locally in axial terms, reaches radially as far as the inner wall of the tubular shaft at at least three circumferential points. This is because, especially in the case of tubular-shaft instruments having a tubular shaft diameter of approximately 3 mm and less, it has become evident that with such thin tubular shafts the force transmitting element also assumes the task of stabilizing the tubular shaft against bending when large tensile forces are being transferred. In the case of the tubular-shaft instrument according to the present invention, this is ensured by the configuration of the force transmitting element by the fact that at least locally, at three circumferential points it reaches radially as far as the inner wall of the tubular shaft, and thereby stabilizes the tubular shaft. In order to ensure that a flushing liquid can pass through in these segments or portions as well, the force transmitting element has in these segments, between the circumferential points toward the inner wall of the tubular shaft, a clearance for the passage of a flushing liquid. Whereas it has been found with the approaches considered in the existing art, i.e. configuring the force transmitting element with a smaller diameter or as a flat strip, that a force transmitting element of this kind jumps back and forth in the tubular shaft as the tubular-shaft instrument is actuated and thus causes bending of the tubular shaft, such jumping back and forth is prevented, in the case of the force transmitting element according to the present invention, by the circumferential points that reach radially as far as the inner wall of the tubular shaft. At the same time, the force transmitting element of the tubular-shaft instrument according to the present invention is itself of more stable configuration and thus can transfer greater tensile forces than a tension strip or a thin wire. In the simplest case, the force transmitting element according to the present invention can be of approximately triangular configuration in cross section in the axial portions at which the force transmitting element reaches to the inner wall of the tubular shaft. The tubular-shaft instrument according to the present invention is easy to clean due to the continuous flushing conduit present between the force transmitting element and the tubular shaft, and no loss of stability of the tubular shaft occurs despite the presence of the continuous flushing space.

The object of the invention is thereby completely achieved.

In a preferred embodiment, the at least three circumferential points reaching radially as far as the inner wall of the tubular shaft extend continuously over the entire region of the force transmitting element extending through the tubular shaft.

With this embodiment, the at least three circumferential points extend not only locally over the force transmitting element, but rather over the entire region of the force transmitting element extending in the tubular shaft. The advantage achieved thereby is that the tubular shaft experiences stabilization by the force transmitting element over its entire length. A further advantage is that manufacture of the force transmitting element is simplified. For example, the force transmitting element can be manufactured from a solid cylindrical material by introducing at least three continuous flattened areas or depressions in the axial direction with a material-removing method, for example by laser techniques or electrodischarge machining, or with a non-material-removing method, for example by rolling or profile drawing, i.e. shaping by drawing a round material through a corresponding die.

In a further preferred embodiment, the force transmitting element is rounded at the at least three circumferential points.

The advantage here is that the at least three circumferential points of the force transmitting element reaching as far as the inner wall of the tubular shaft do not cut into the inner wall of the tubular shaft during long-term use of the tubular-shaft instrument, as might possibly be the case with sharp edges.

It is preferred in this context if the radius of curvature of the circumferential points is smaller than the inside radius of the tubular shaft.

The advantage here is that the force transmitting element rests with its at least three circumferential points in only linear fashion against the inner wall of the tubular shaft, thus minimizing friction during the axial back-and-forth movement of the force transmitting element in the tubular shaft as the tubular-shaft instrument is used. In addition, the flushing cross section available between the force transmitting element and the tubular shaft for the passage of a flushing liquid is enlarged, and the regions between the outer contour of the force transmitting element and the inner wall of the tubular shaft that are difficult for the flushing liquid to access are minimized.

In a further preferred embodiment, the force transmitting element is concavely recessed, viewed toward the longitudinal center axis of the force transmitting element, between the at least three circumferential points.

The advantage here is that the flushing cross section usable for the passage of a flushing liquid can be even further enlarged, without loss of stability, as compared to an embodiment in which the cross section of the force transmitting element has the shape of a triangle with straight sides, so that the ability of the tubular-shaft instrument according to the present invention to be cleaned is further improved.

In a further preferred embodiment, the at least three circumferential points reaching radially as far as the inner wall of the tubular shaft extend in straight-line fashion.

It is advantageous in this context that the force-transfer element can be easily manufactured, although consideration can also be given to having the at least three aforesaid circumferential points run in helical fashion around the longitudinal center axis of the force transmitting element.

In a further preferred embodiment, the at least three circumferential points assume an identical angular spacing from one another.

This embodiment achieves optimum symmetrical bracing of the force transmitting element on all sides against the inner wall of the tubular shaft.

The embodiment of the tubular-shaft instrument according to the present invention can be used both with a forceps for cutting and/or grasping and with a needle holder.

Further advantages are evident from the description below and the appended drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

Exemplary embodiments of the invention are shown in the drawings and will be explained in more detail in the description below. In the drawings:

FIG. 2 shows a cross section along line II—II in FIG. 1, at enlarged scale;

FIG. 3 shows a cross section, corresponding to FIG. 2, which shows the existing art;

FIG. 4 shows a section along line IV—IV in FIG. 2, in a portion of the tubular-shaft instrument in FIG. 1 that is labeled A in FIG. 1.

DETAILED DESCRIPTION OF PREFERRED EMBODIMENT

Figure 1:
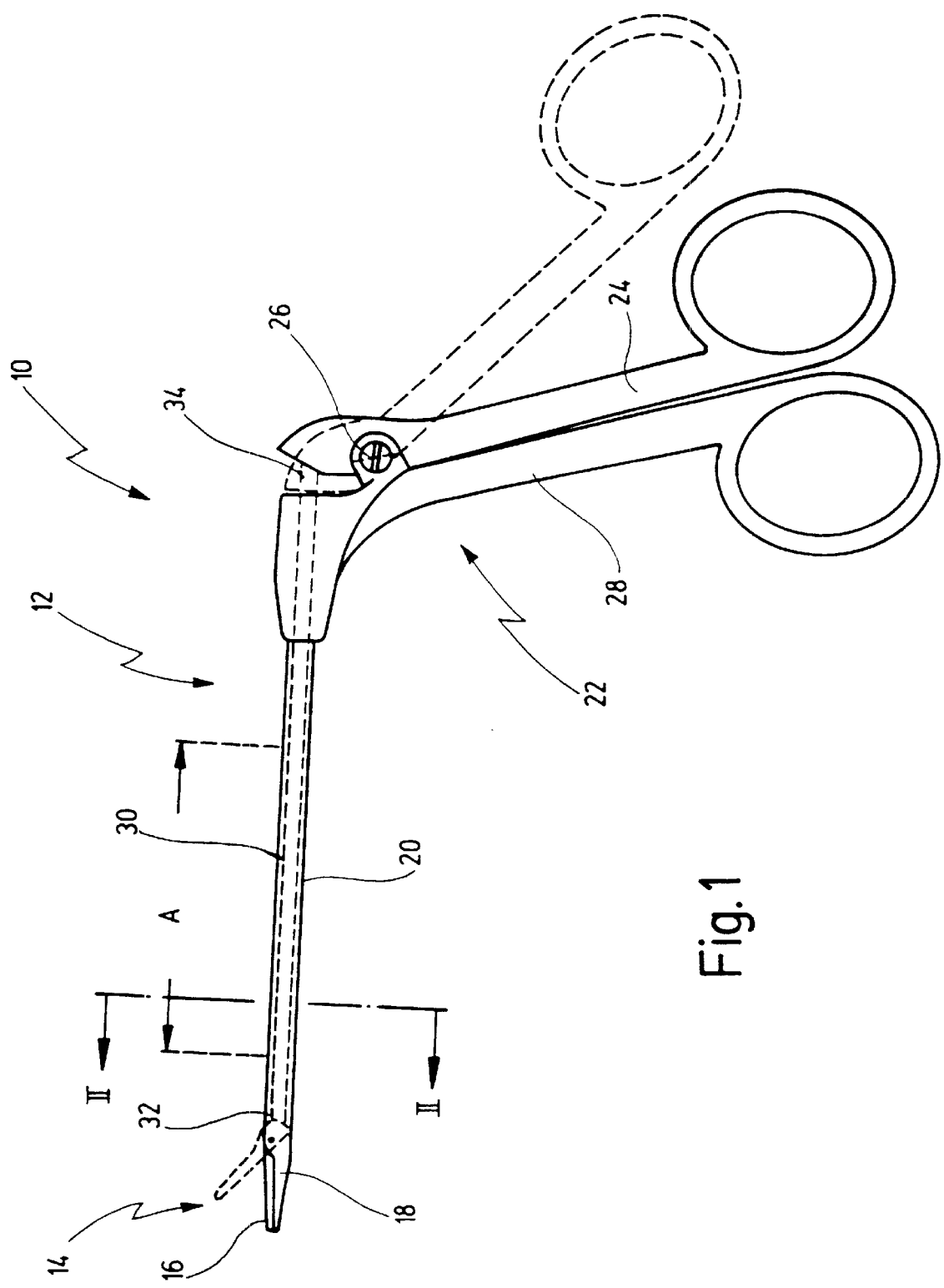
FIG. 1 shows a side view of a medical tubular-shaft instrument according to a first exemplary embodiment.

FIG. 1 shows a medical tubular-shaft instrument labeled with the general reference character 10. In the exemplary embodiment shown, medical tubular-shaft instrument 10 is a medical forceps 12 for cutting tissue in the human or animal body.

Forceps 12 has at the distal end at least one movable tool 14. Tool 14 is a movable jaw part 16 that coacts in cutting fashion with a further jaw part 18 which is in this case stationary but can also be movable.

The two jaw parts 16 and 18 are mounted at the distal end of a tubular shaft 20. Tubular shaft 20 is of hollow cylindrical configuration. In the present case tubular shaft 20 has an outside diameter of approximately 3 mm or less. Tubular shaft 20 is furthermore rigid.

At the proximal end of tubular shaft 20, a handle 22 is immovably joined to it. Handle 22 has at least one movable grip element 24 that serves to actuate the at least one movable tool 14, i.e. in this case the one jaw part 16.

Movable grip element 24 is joined in articulated fashion, via a joint 26, to a stationary grip element 28 immovably joined to tubular shaft 20.

A force transmitting element 30, which is indicated in FIG. 1 with dashed lines and is shown in more detail in FIGS. 2 and 4, is provided for force transmitting from movable grip element 24 to movable jaw part 16.

Force transmitting element 30 is interposed between the at least one movable tool 14, i.e. in this case movable jaw part 16, and the at least one movable grip element 24. More precisely, a distal end 32 of force transmitting element 30 is joined to movable jaw part 16, and a proximal end 34 of force transmitting element 30 to movable grip element 24. Force transmitting element 30 extends through tubular shaft 20, i.e. is arranged in tubular shaft 20.

Force transmitting element 30 operates in tension to close jaw parts 16 and 18, i.e. from the open position of movable jaw part 16 shown with dashed lines in FIG. 1, which corresponds to the position of movable grip element 24 shown with dashed lines, movement of movable grip element 24 toward stationary grip element 28 causes force transmitting element 30 to be pulled in the proximal direction in tubular shaft 20, as a result of which movable jaw part 16 is closed against stationary jaw part 18.

As is evident from FIGS. 2 and 4, which depict the force transmitting element in cross section and in longitudinal section at enlarged scale, force transmitting element 30 has, at least in its region extending through tubular shaft 20, an outer contour 36 that, at least locally in axial terms, reaches radially at at least three circumferential points (labeled 38, 40, and 42 in FIG. 2) as far as an inner wall 44 of tubular shaft 20, and as a result guarantees bracing of tubular shaft 20 on all sides.

As shown in FIG. 4, the at least three circumferential points 38, 40, and 42 are provided on two axial portions 46 and 48 of force transmitting element 30. Since FIG. 4 shows only an axial portion of tubular shaft 20 and of force transmitting element 30, however, it is understood that a greater number of portions of this kind can be provided, at least in the region of force transmitting element 30 extending through tubular shaft 20.

In portions 46 and 48, circumferential points 38, 40, and 42 reaching radially to the inner wall 44 of tubular shaft 20 extend over an axial partial length of force transmitting element 30. In the remaining portions, in which force transmitting element 30 has no circumferential points reaching as far as inner wall 44 of tubular shaft 20 and bracing against the latter, force transmitting element 30 has at least over part of its circumference a clearance from inner wall 44, as is shown in FIG. 4 by way of example with a portion 50, in which force transmitting element 30 has on all sides a clearance from inner wall 44 of tubular shaft 20. Whereas force transmitting element 30 has, in portions 46 and 48 and in the further portions corresponding to those portions, a substantially triangular cross section, force transmitting element 30 can have, in portion 50 and in the further portions corresponding to said portion 50, a substantially round cross section, the round cross section in portion 50 and in the further portions corresponding to said portion 50 having a smaller diameter than inner wall 44 of tubular shaft 20.

Instead of providing the at least three circumferential points 38, 40, and 42 on force transmitting element 30 only locally in axial terms, it is preferred if circumferential points 38, 40, and 42 that brace against inner wall 44 of tubular shaft 20 extend continuously over the entire region of force transmitting element 30 that extends through tubular shaft 20. This is shown in FIG. 4 with dashed lines. In other words, transfer element 30 then has, at any given axial position force, a cross section like the one shown in FIG. 2.

Circumferential points 38, 40, 42, configured in the manner of flanges, extend between proximal end 34 and distal end 32 in a straight line. A helical configuration can, however, also be provided.

Between circumferential points 38, 40, and 42, outer contour 36 of force transmitting element 30 has in each case a clearance radially from inner wall 44 of tubular shaft 20. There is thus present in each case between circumferential points 38, 40, and 42, resting against inner wall 44 of tubular shaft 20, a cavity 52, 54, 56 that serves as a flushing conduit for the passage of a flushing liquid. Cavities 52, 54, 56 usable as flushing conduits thus extend over the entire length of the region of force transmitting element 30 arranged in tubular shaft 20.

Force transmitting element 30 is rounded at circumferential points 38, 40, 42, the radius of curvature of circumferential points 38, 40, 42 being smaller than the inside radius of tubular shaft 20.

In addition, outer contour 36 of force transmitting element 30 has, between circumferential points 38, 40, 42, a depression that is concave viewed toward the longitudinal center axis of force transmitting element 30, as a result of which the flushing cross section in cavities 52, 54, 56 is enlarged.

Circumferential points 38, 40, and 42 moreover have an angular spacing of approximately 120° from one another in each case, i.e. they are at identical angular spacings from one another, thus achieving a uniform bracing of force transmitting element 30 on all sides against inner wall 44 of tubular shaft 20.

Force transmitting element 30 is manufactured overall in solid fashion from a solid material, for example from a cylindrical body in which depressions are introduced over part of the circumference by material-removing shaping, for example using a laser method or an electrodischarge method, into the outer contour as shown in the configuration in FIG. 2. As an alternative to this, force transmitting element 30 can also be manufactured with the shape shown using a non-material-removing method, by rolling or by profile drawing, i.e. drawing by pulling a round material through a corresponding die, the latter preferably being utilized.

FIG. 3, on the other hand, shows an embodiment of a force transmitting element 30' known from the existing art, arranged in a tubular shaft 20'. This conventional force transmitting element 30' is configured, like the interior of tubular shaft 20', with a round cross section, the diameter of force transmitting element 30' being substantially identical to the inside diameter of tubular shaft 20'. Accordingly, no room is present between force transmitting element 30' and tubular shaft 20' for the passage of a flushing liquid, i.e. the interior of tubular shaft 20' cannot be flushed. If force transmitting element 30' were flattened on both sides into a strip on two opposite circumferential sides, as far as the dashed lines shown in FIG. 3, the arrangement made up of force transmitting element 30' and tubular shaft 20' would suffer from a considerable loss of stability. Upon actuation of force transmitting element 30', the result of a configuration of this kind flattened on both sides would be that force transmitting element 30' would jump back and forth in tubular shaft 20', especially when greater tensile forces were being transferred, so that tubular shaft 20' might bend. With a configuration of force transmitting element 30' flattened on both sides, a flushing space would therefore exist, but a tubular-shaft instrument of this kind would not withstand the occasionally high applied forces over the long term.

With the configuration according to the present invention of force transmitting element 30 shown in FIG. 2, however, on the one hand a sufficient flushing cross section is created between force transmitting element 30 and tubular shaft 20, and on the other hand circumferential points 38, 40, and 42 reaching radially as far as inner wall 44 of tubular shaft 20 prevent force transmitting element 30 from jumping back and forth in response to alternating tensile and compressive stresses, thus stabilizing tubular shaft 20 so that the latter does not bend even when exposed to large applied forces.

Figure 5:
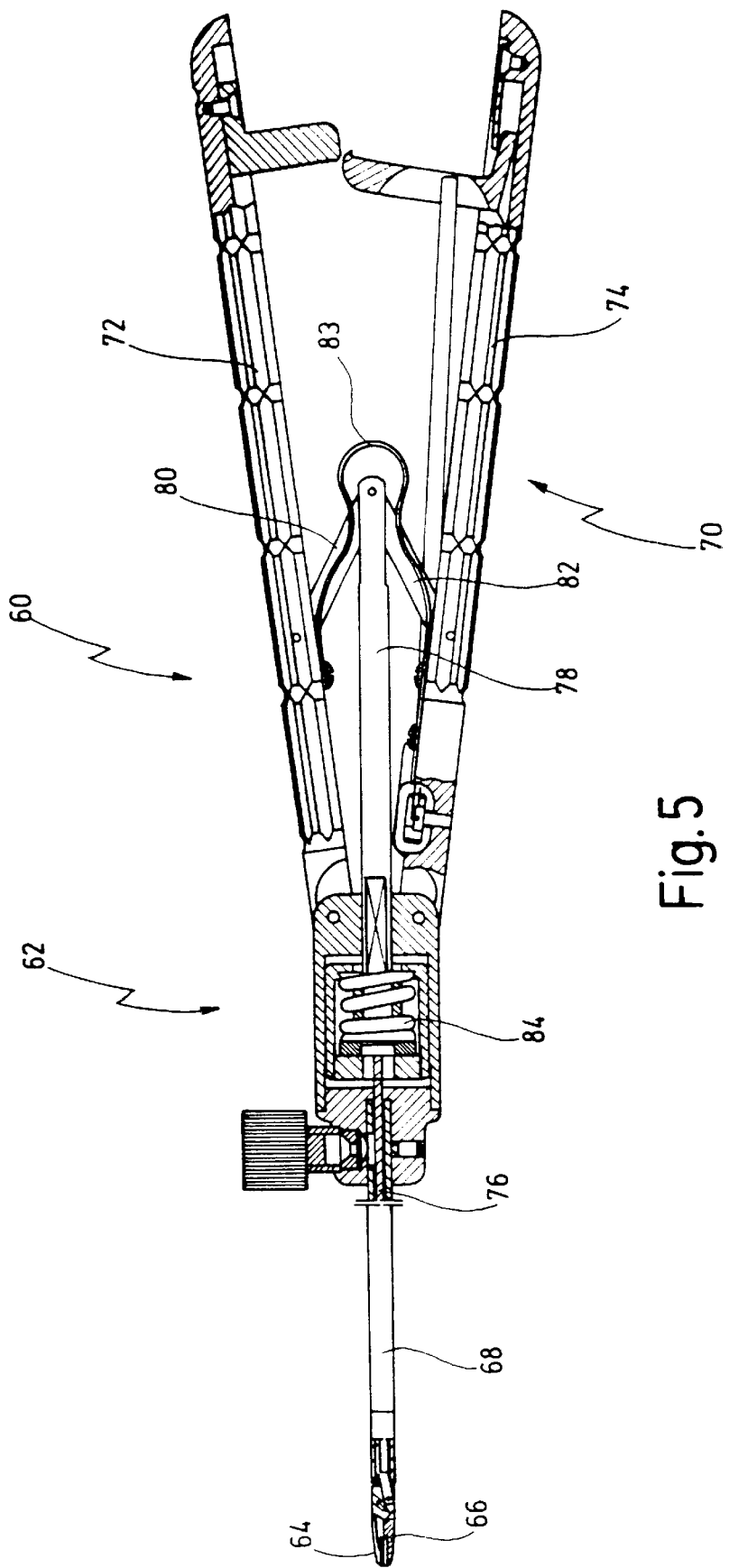
FIG. 5 shows a side view of a tubular-shaft instrument according to a further exemplary embodiment.

FIG. 5 shows, in accordance with a further exemplary embodiment, a medical tubular-shaft instrument 60 in the form of a needle holder 62 in which the invention is also advantageously utilized.

Needle holder 62 is used to hold a needle and guide it through the tissue in order to join tissue by way of a suture. For that purpose, needle holder 62 has at its distal end two movable tools 64 and 66 in the form of two forceps-like jaw parts with which a needle (not shown) can be held securely and immovably and can be guided. The two movable tools 64 and 66 are arranged at the distal end of a tubular shaft 68 at whose proximal end is once again arranged a handle 70 that in this case has two movable grip elements 72 and 74.

Movable tools 64 and 66 are nonpositively joined to movable grip elements 72 and 74 by way of a force transmitting element 76 that extends through tubular shaft 68, and by way of a lever linkage that is joined to force transmitting element 76 and is made up of an axial rod 78 and two pivot levers 80 and 82. Axial rod 78 is preloaded into its maximally distal position by a leaf spring 83 that engages on grip elements 72 and 74 and is mounted close to pivot levers 80 and 82. A compression spring 84 serves as an overload protector that takes effect if excessive force is exerted on grip elements 72 and 74.

Pressing grip elements 72 and 74 together causes axial rod 78 to be displaced in the proximal direction against the action of leaf spring 83, as a result of which force transmitting element 76 joined to axial rod 78 is also displaced in the proximal direction in order to close tools 64 and 66.

According to the present invention, force transmitting element 76 has, in its region extending through tubular shaft 68, a configuration like that provided according to FIG. 2 for the exemplary embodiment of tubular-shaft instrument 10 described earlier. An improved capability for cleaning thus exists for needle holder 62 as well, since on the one hand a flushing liquid can pass between force transmitting element 76 and tubular shaft 68 in order to flush the interior of tubular shaft 68. On the other hand, however, the stability of tubular shaft 68 is not thereby degraded, i.e. the latter is protected against bending in the manner already explained with reference to the previous exemplary embodiment.

What is claimed is:

1. A medical tubular-shaft instrument, comprising:
   an elongated tubular shaft having a distal end and a proximal end, and having an inner wall;
   at least one tool disposed at said distal end of said shaft;
   least one movable grip element disposed at said proximal end of said shaft;
   an elongated reciprocal force transmitting element for transmitting either compressive or tensile forces from said movable grip element to said at least one tool, said force transmitting element having a distal end which is operatively connected to said at least one too, and a proximal end which is operatively connected to said at least one movable grip element, said force transmitting element extending through a length of said tubular shaft,
   said force transmitting element further comprises, in at least two localized areas, at least three circumferential points extending radially towards said inner wall of said shaft; and
   said force transmitting element further comprises a clearance extending axially between said at least three circumferential points and said inner wall.

2. The tubular-shaft instrument of claim 1, wherein said at least three circumferential points extends axially and continuously over the entire length of said force transmitting element.

3. The tubular-shaft instrument of claim 1, wherein said force transmitting element comprises a rounded cross section in at least one localized area.

4. The tubular-shaft instrument of claim 3, wherein an outermost radius of said circumferential points is less than an inside radius of said tubular shaft.

5. The tubular-shaft instrument of claim 1, wherein said force transmitting element further comprises a recess between each of said at least three circumferential points.

6. The tubular-shaft instrument of claim 1, wherein said at least three circumferential points extends axially in a generally straight-line.

7. The tubular-shaft instrument of claim 1, wherein said at least three circumferential points are angularly oriented equidistant from one another.

8. The tubular-shaft instrument of claim 1, wherein the instrument is a forceps for cutting and grasping.

9. The tubular-shaft instrument of claim 1, wherein the instrument is a needle holder.

10. The tubular shaft instrument of claim 1, wherein said clearance is for flushing the instrument.

* * * * *